United States Patent
Mizuno

(10) Patent No.: US 7,416,303 B2
(45) Date of Patent: Aug. 26, 2008

(54) OPHTHALMIC OBSERVATION APPARATUS

(75) Inventor: Katsuyasu Mizuno, Gamagori (JP)

(73) Assignee: Nidek Co. Ltd., Gamagori (JP)

( * ) Notice: Subject to any disclaimer, the term of this patent is extended or adjusted under 35 U.S.C. 154(b) by 362 days.

(21) Appl. No.: 11/210,793

(22) Filed: Aug. 25, 2005

(65) Prior Publication Data

US 2006/0055885 A1  Mar. 16, 2006

(30) Foreign Application Priority Data

Aug. 31, 2004  (JP) .............................. 2004-251328

(51) Int. Cl.
*A61B 3/14* (2006.01)
*A61B 3/10* (2006.01)

(52) U.S. Cl. ...................... 351/210; 351/205

(58) Field of Classification Search .................. 351/210
See application file for complete search history.

(56) References Cited

U.S. PATENT DOCUMENTS 4,893,920 A * 1/1990 Webb .......................... 351/221
5,177,511 A 1/1993 Feuerstein et al.
5,396,302 A 3/1995 Triller et al.
2004/0156016 A1 * 8/2004 Kerr et al. .................... 351/206

FOREIGN PATENT DOCUMENTS

JP  A 07-178053  7/1995

* cited by examiner

*Primary Examiner*—Scott J. Sugarman
*Assistant Examiner*—Dawayne A Pinkney
(74) *Attorney, Agent, or Firm*—Oliff & Berridge, PLC

(57) ABSTRACT

An ophthalmic observation apparatus for observing an object region to be observed of an examinee's eye, comprises: an illumination optical system which has a laser source, a polygon mirror, and a galvano mirror, and which irradiates the object region with a laser beam emitted from the laser source by scanning the laser beam in two dimensions by use of the polygon mirror and the galvano mirror; a photo-receiving optical system which has a beam splitter placed on an optical path between the eye and the polygon mirror, and a photo-receiving element placed in a conjugate position with a pupil of the eye, the photo-receiving element being arranged to receive the laser beam reflected from the object region via the beam splitter, not via the polygon mirror; and an image processing part which processes an output signal from the photo-receiving element in sync with scanning operations of the polygon mirror and the galvano mirror to generate an observation image of the object region.

6 Claims, 4 Drawing Sheets

OPHTHALMIC OBSERVATION APPARATUS

BACKGROUND OF THE INVENTION

1. Field of the Invention

The present invention relates to an ophthalmic observation apparatus for observing an examinee's eye.

2. Description of Related Art

There is an apparatus arranged to obtain an observation image of an object region to be observed by irradiating the object region with a laser beam by scanning the laser beam in two dimensions, and receiving the laser beam reflected from the object region by use of a photo-receiving element (a photodetector). Such apparatus comprises a scanning optical system having a polygon mirror and a galvano mirror for irradiating the object region with the laser beam by scanning the laser beam in two dimensions. The laser beam reflected from the object region is received by the photo-receiving element through the scanning optical system so that an output signal from the photo-receiving element is processed in sync with scanning operations of the scanning optical system. Thus, the observation image of the object region is generated.

For observation of the object region by the above manner, it is necessary to achieve the observation image of the object region in a form of smoothly moving images of a high resolution.

SUMMARY OF THE INVENTION

The present invention has an object to provide an ophthalmic observation apparatus capable of generating smoothly moving images of a high resolution as an observation image of an object region to be observed without needing a complicated and large-sized optical system.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the purpose of the invention, there is provided an ophthalmic observation apparatus for observing an object region to be observed of an examinee's eye, comprising: an illumination optical system which has a laser source, a polygon mirror, and a galvano mirror, and which irradiates the object region with a laser beam emitted from the laser source by scanning the laser beam in two dimensions by use of the polygon mirror and the galvano mirror; a photo-receiving optical system which has a beam splitter placed on an optical path between the eye and the polygon mirror, and a photo-receiving element placed in a conjugate position with a pupil of the eye, the photo-receiving element being arranged to receive the laser beam reflected from the object region via the beam splitter, not via the polygon mirror; and an image processing part which processes an output signal from the photo-receiving element in sync with scanning operations of the polygon mirror and the galvano mirror to generate an observation image of the object region.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings.

DETAILED DESCRIPTION OF THE PREFERRED EMBODIMENTS

Figure 1:
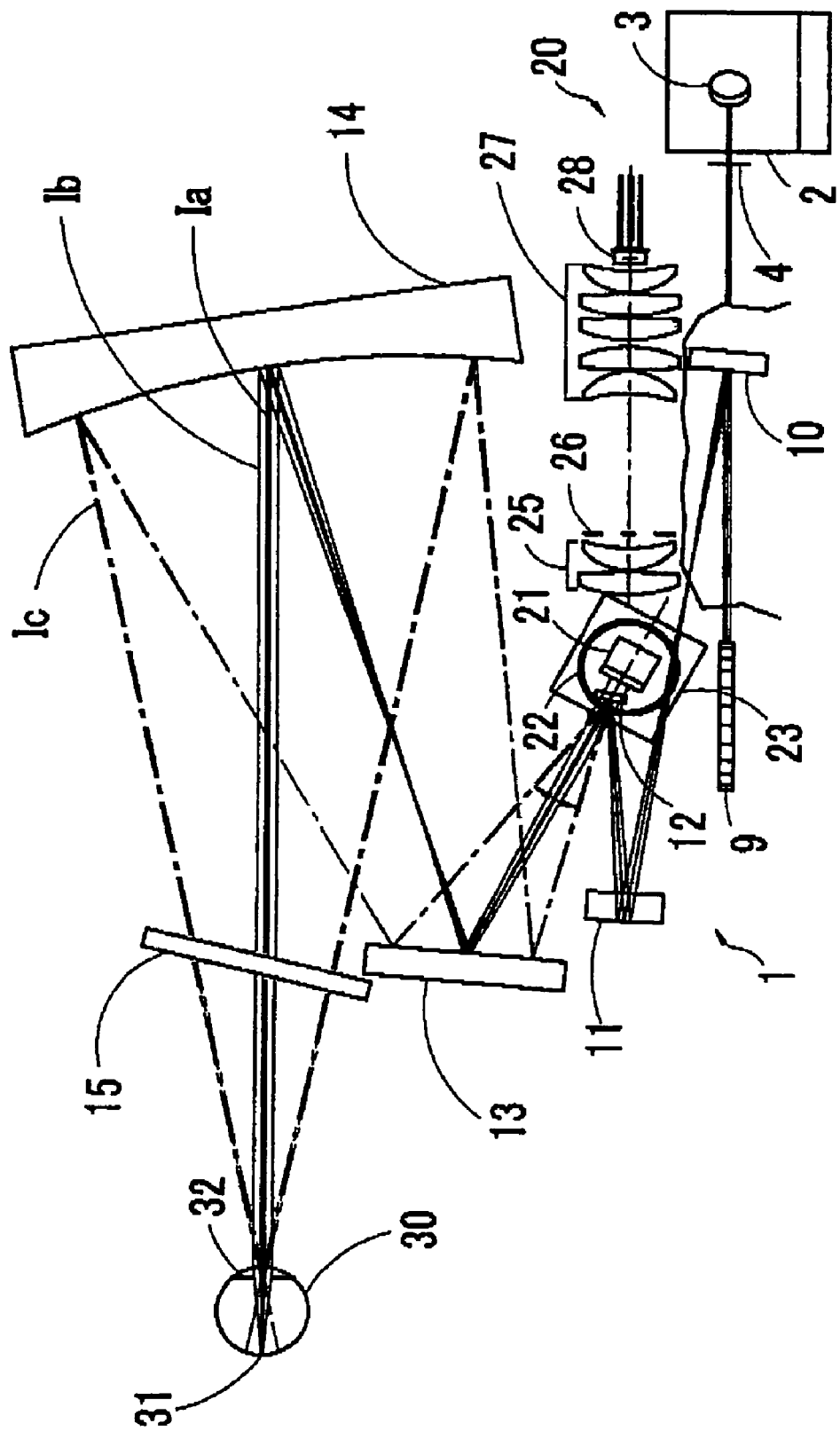
FIG. 1 is a schematic structural view of optical systems of an ophthalmic observation apparatus in a present embodiment of the invention, the optical systems being seen from side.
Figure 2:
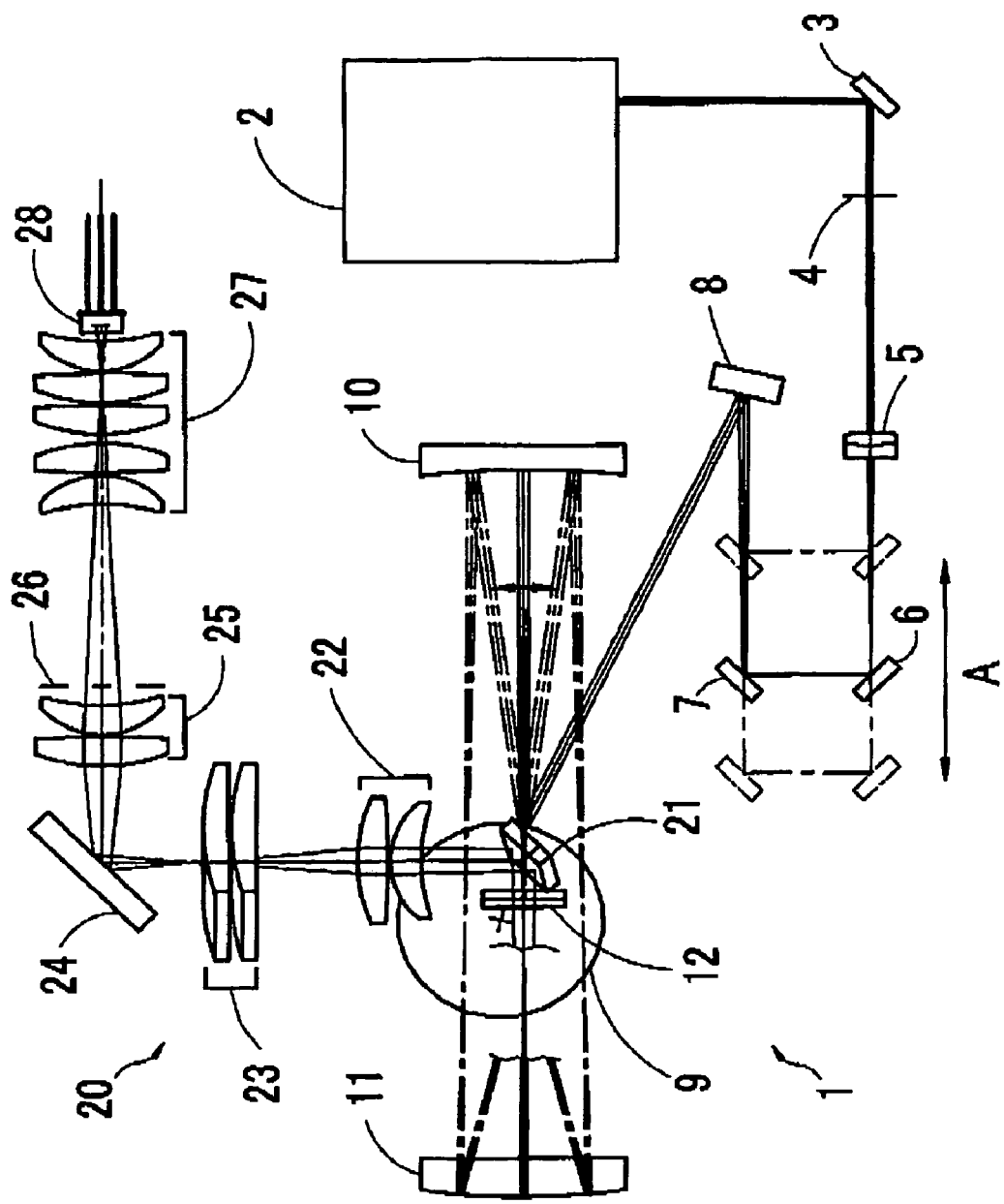
FIG. 2 is a schematic structural view of part of the optical systems shown in FIG. 1, the optical systems being seen from top.
Figure 3:
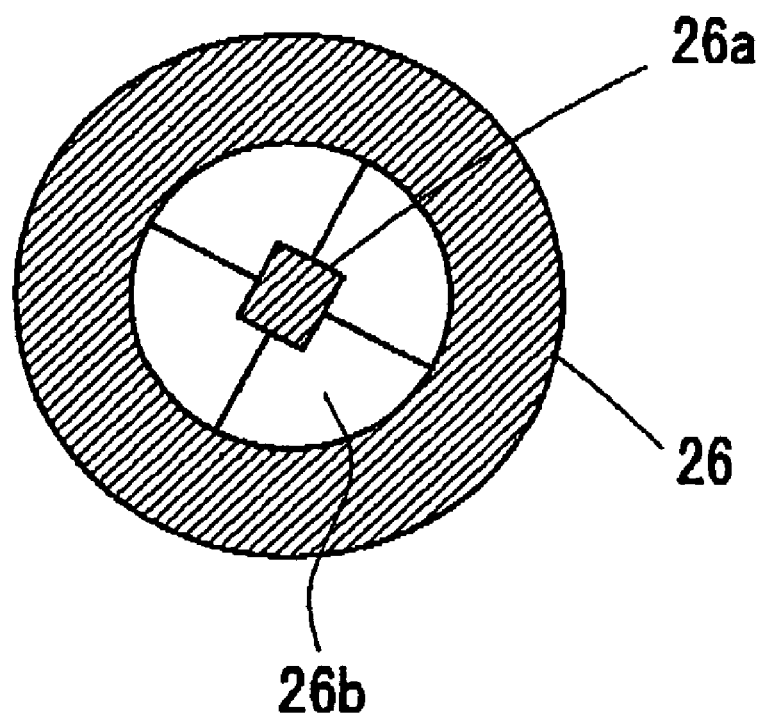
FIG. 3 is a schematic structural view of a shielding plate.
Figure 4:
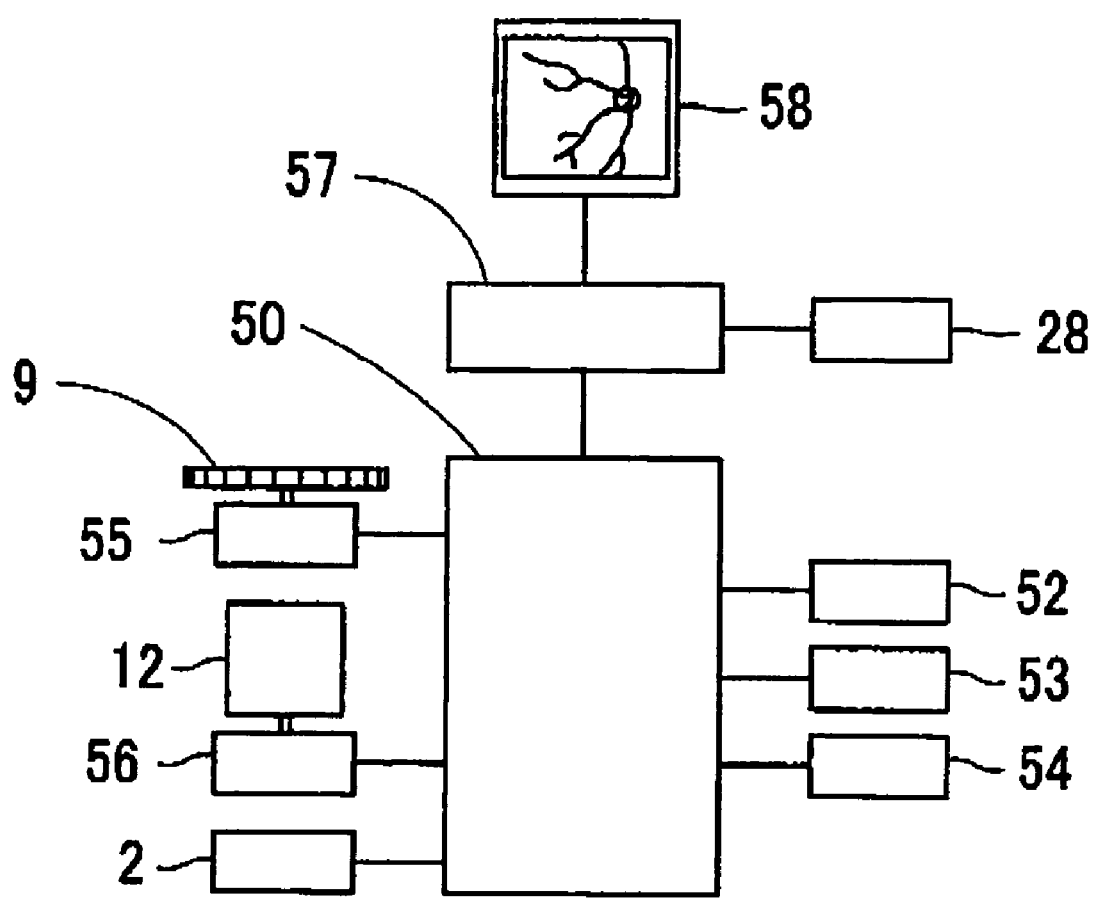
FIG. 4 is a block diagram showing a schematic structure of a control system of the observation apparatus.

A detailed description of a preferred embodiment of the present invention will now be given referring to the accompanying drawings. FIG. 1 is a schematic structural view of optical systems of an ophthalmic observation apparatus in the present embodiment, the optical systems being seen from side; FIG. 2 is a schematic structural view of part of the optical systems shown in FIG. 1, the optical systems being seen from top; FIG. 3 is a schematic structural view of a shielding plate mounted in the optical system shown in FIG. 1 and 2; and FIG. 4 is a block diagram showing a schematic structure of a control system of the observation apparatus.

Numeral 1 denotes an illumination optical system (a laser irradiation optical system) and numeral 20 denotes a photo-receiving optical system (an observation optical system). Alphabetical sign "Ia" represents a laser beam to be irradiated to an object region to be observed, that is, a fundus 31 of an examinee's eye 30; "Ib" represents a laser beam reflected from the fundus 31; and "Ic" represents a scanning area of the laser beam on an optical path.

A laser source 2 has a semiconductor laser which emits a laser beam of a wavelength of 785 nm. The laser beam emitted from the laser source 2 falls on a polygon mirror 9 via a plane mirror 3, a diaphragm 4, a convex lens 5, plane mirrors 6 and 7, and a concave lens 8 in this order. The plane mirrors 6 and 7 are movable in an optical axis direction (in a direction indicated by an arrow A) for diopter correction. The laser beam reflected from the polygon mirror 9 then falls on a galvano mirror 12 via concave mirrors 10 and 11 in turn. The laser beam reflected by the galvano mirror 12 enters the eye 30 via a plane mirror 13, a concave mirror 14, and a window 15 and then is focused on the fundus 31. The laser beam is scanned in right-and-left (horizontal) directions with respect to the eye 30 according to rotation of the polygon mirror 9 and in up-and-down (vertical) directions with respect to the eye 30 according to oscillation (swing) of the galvano mirror 12. Thus, the laser beam is scanned in two dimensions to be irradiated to the fundus 31.

The galvano mirror 12 is placed in a conjugate position with a pupil 32 of the eye 30 via the plane mirror 13 and the concave mirror 14. The polygon mirror 9 is placed in a conjugate position with the pupil 32 via the concave mirror 10 through the concave mirror 14. The diaphragm 4 is placed in a conjugate position with the pupil 32 via the convex lens 5 through the concave mirror 14. It is to be noted that the "conjugate" in the present specification needs no strict conjugate but has to include a conjugate relation enough to provide the accuracy needed for generating an observation image of the fundus.

The laser beam to be irradiated to the fundus 31 is formed (focused) by the diaphragm 4 to have a beam diameter of about 2 mm on a reflection surface of the polygon mirror 9 and a beam diameter of about 1 mm on the pupil 32 when the laser beam enters the eye 30. The concave mirror 11 serves as a back-side mirror for correcting aberration caused by the concave mirror 14.

The laser beam reflected from the fundus 31 returns to the galvano mirror 12 via the window 15, the concave mirror 14, and the plane mirror 13 and then falls on the galvano mirror 12 again. The galvano mirror 12 in the present embodiment is a semi-transparent mirror (half mirror) with a dielectric film deposited on a reflection surface. It is preferable for this galvano mirror 12 to have the optical property that transmittance is larger than reflectance. As to the galvano mirror 12 in the present embodiment, for instance, a ratio of transmittance to reflectance is 7 to 3. After passing through the galvano mirror 12, the reflected beam from the fundus 31 falls on a cylindrical lens 23 via a plane mirror 21 and a lens 22, thereby correcting the aberration caused by the concave mirror 14. This beam then falls on a shielding plate 26 via a plane mirror 24 and a lens 25. The shielding plate 26 is placed in a conjugate position with the pupil 32 or a cornea of the eye 30 and is provided with a rectangular shielding part 26a at the center and further an opening part 26b surrounding the shielding part 26a. The shielding plate 26 is arranged so that the shielding part 26a removes the beam reflected from the cornea of the eye 30 and the opening part 26b allows the reflected beam from the fundus 31 to pass through it. In the present embodiment, the shielding part 26a is designed at a horizontal to vertical ratio equal to that of the scanning area of the laser beam to be scanned in two dimensions in order to efficiently remove the beam reflected from the cornea and achieve the maximum light amount of the reflected beam from the fundus 31 which is picked up from the peripheral portion of the pupil 32 (i.e., the opening part 26b). The reflected beam from the fundus 31, which is picked up from the peripheral portion of the pupil 32, is received by a photo-receiving element 28 placed in a conjugate position with the pupil 32 through a lens 27.

In the present embodiment, the photo-receiving element 28 is an avalanche photodiode (APD) having a diameter of 3 mm. When placed in the conjugate position with the pupil 32, the photo-receiving element 28 can receive the reflected beam from the fundus 31 even if a photo-receiving surface is the same in size as the reflected beam to be picked up from the peripheral portion of the pupil 32.

Connected to a control section 50 for controlling the entire apparatus are the laser source 2, a moving unit 52 for moving the plane mirrors 6 and 7, a controller 53, a storage part 54, a rotating unit 55 for rotating the polygon mirror 9, an oscillating unit 56 for oscillating the galvano mirror 12, an image processing part 57, etc. Furthermore, connected to the image processing part 57 are a monitor 58 for displaying an observation image of a fundus, the photo-receiving element 28, etc.

For observation of the fundus, the refractive power of the eye 30 is measured in advance with an eye refractive power measuring apparatus or the like. The measured refractive power data is input with the controller 53. The control section 50 stores the input refractive power data in the storage part 54 and also controls the moving unit 52 based on the refractive power data to move the plane mirrors 6 and 7, thereby performing diopter (refractive power) correction of the eye 30.

The laser beam emitted from the laser source 2 travels along the illumination optical system 1 into the eye 30 through the center portion of the pupil 32. The laser beam is then scanned to irradiate the fundus 31. The laser beam reflected from the fundus 31 passes through the galvano mirror 12 via the window 15 through the plane mirror 13. After passing through the galvano mirror 12, the reflected beam from the fundus 31 is received by the photo-receiving element 28 via the plane mirror 21 through the lens 27. The image processing part 57 processes the output signal from the photo-receiving element 28 in sync with the scanning operations of the polygon mirror 9 and the galvano mirror 12 to generate a two-dimensional image of the fundus 31, namely, a fundus observation image, and displays it in a form of moving images on the monitor 58.

Herein, in a conventional structure that receives a reflected beam from the fundus 31 via the polygon mirror 9, the reflected beam from the fundus 31 is increased (thickened) in beam diameter by three or five times larger than the irradiation beam to the fundus 31. Accordingly, the width of each reflection surface of the polygon mirror 9 has to be increased (widened) proportionally. For instance, if the irradiation beam is designed to have a beam diameter of about 1 mm at the time of entering the pupil 32, the beam diameter of the irradiation beam to the fundus 31 is about 2 mm at the time of falling on the reflection surface of the polygon mirror 9, whereas the beam diameter of the reflected beam from the fundus 31 is about 6 mm at the time of falling on the reflection surface of the polygon mirror 9. Hence, each reflection surface of the polygon mirror 9 needs a wider width. In the present embodiment, in contrast, the reflected beam from the fundus 31 will not fall on the polygon mirror 9 again. Accordingly, each reflection surface of the polygon mirror 9 is required only to have a width enough to reflect the irradiation beam to the fundus 31. In the present embodiment, therefore, the polygon mirror 9 having reflection surfaces each having a smaller width than the beam diameter of the reflected beam from the fundus 31 can be used. The polygon mirror 9 can be rotated at a higher speed by just that much. When the rotating speed of the polygon mirror 9 can be increased, resolution (the number of pixels) of one picture can be increased without a decrease in frame rate.

The frame rate of an image is determined depending on the number of oscillations of the galvano mirror 12. Further, the resolution of one picture in a vertical direction (the number of horizontal scanning lines) is determined based on the number of reflection surfaces of the polygon mirror 9 and the rotating speed (revolutions per second) thereof and the number of oscillations of the galvano mirror 12. For instance, if the galvano mirror 12 is oscillated at 30 Hz and the polygon mirror 9 having 24 reflection surfaces is rotated in order to generate 30 images per second, each having 480 pixels high by 640 pixels wide, the polygon mirror 9 has to be rotated at a rotating speed of 480×30/24=600 rev/sec (that is, 36,000 rpm). This is a speed at which even a conventional sized polygon mirror can be rotated. On the other hand, in order to generate 30 images per second, each having 600 pixels high by 800 pixels wide, the polygon mirror 9 has to be rotated at a rotating speed of 600×30/24=750 rev/sec (that is, 45,000 rpm). This is a speed at which a polygon mirror if reduced in weight can be rotated. The image of 800 pixels wide is sufficiently achieved if a sampling time of the output signal from the photo-receiving element 28 is appropriately controlled.

In the present embodiment, the galvano mirror 12 is a semi-transparent mirror to serve as a beam splitter for guiding the reflected beam from the fundus 31 to the photo-receiving element 28 placed on an optical path different from an optical path directed to the polygon mirror 9, but the galvano mirror 12 is not limited thereto. For instance, an additional semi-transparent mirror may be placed on an optical path between the eye 30 and the polygon mirror 9 to guide the reflected beam from the fundus 31 to the photo-receiving element 28. The galvano mirror 12 may be structured in any form, instead of using a semi-transparent mirror. For example, it is possible that a centrally-located strip portion which the irradiation beam to the fundus 31 falls on has the total reflection property by chrome deposition or others and another portion which the reflected beam from the fundus 31 falls on, excluding the central portion, has the total transmission property.

While the presently preferred embodiment of the present invention has been shown and described, it is to be understood that this disclosure is for the purpose of illustration and that various changes and modifications may be made without departing from the scope of the invention as set forth in the appended claims.

What is claimed is:

1. An ophthalmic observation apparatus for observing an object region to be observed of an examinee's eye, comprising:

an illumination optical system which has a laser source, a polygon mirror, and a galvano mirror, and which irradiates the object region with a laser beam emitted from the laser source by scanning the laser beam in two dimensions by use of the polygon mirror and the galvano mirror;

a photo-receiving optical system which includes the galvano mirror configured as a beam splitter placed on an optical path between the eye and the polygon mirror, and a photo-receiving element placed in a conjugate position with a pupil of the eye, the photo-receiving element being arranged to receive the laser beam reflected from the object region via the beam splitter, not via the polygon mirror; and an image processing part which processes an output signal from the photo-receiving element in sync with scanning operations of the polygon mirror and the galvano mirror to generate an observation image of the object region.

2. The ophthalmic observation apparatus according to claim 1, wherein the polygon mirror has reflection surfaces each of which has a width determined according to a beam diameter of the laser beam determined at the time of falling on each reflection surface, the laser beam being to be irradiated to the eye.

3. The ophthalmic observation apparatus according to claim 1, wherein the photo-receiving optical system includes a shielding plate which includes a shielding part at the center and an opening part surrounding the shielding part and which is placed in a conjugate position with the pupil or a cornea of the eye.

4. The ophthalmic observation apparatus according to claim 3, wherein the shielding part of the shielding plate is of a rectangular shape having a horizontal to vertical ratio equal to that of a scanning area of the laser beam.

5. The ophthalmic observation apparatus according to claim 1, wherein the galvano mirror includes a semi-transparent mirror.

6. The ophthalmic observation apparatus according to claim 1, wherein the galvano mirror is structured such that a portion which the laser beam to be irradiated to the eye falls on has a total reflection property and another portion which the laser beam reflected from the eye falls on has a total transmittance property.

* * * * *